(12) United States Patent
Ogawa et al.

(10) Patent No.: US 10,197,507 B2
(45) Date of Patent: Feb. 5, 2019

(54) INSPECTION APPARATUS

(71) Applicant: NuFlare Technology, Inc., Yokohama (JP)

(72) Inventors: Riki Ogawa, Kanagawa (JP); Hiromu Inoue, Kanagawa (JP); Masatoshi Hirono, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 597 days.

(21) Appl. No.: 14/153,199

(22) Filed: Jan. 13, 2014

(65) Prior Publication Data
US 2014/0204202 A1  Jul. 24, 2014

(30) Foreign Application Priority Data

Jan. 18, 2013  (JP) .................................. 2013-007793

(51) Int. Cl.
*G01R 31/309*  (2006.01)
*G01N 21/956*  (2006.01)
(Continued)

(52) U.S. Cl.
CPC ....... *G01N 21/956* (2013.01); *G01N 21/9503* (2013.01); *B82Y 40/00* (2013.01); *G01N 2021/8848* (2013.01)

(58) Field of Classification Search
CPC ............. G01N 21/9501; G01N 21/956; G01N 21/95607; G01N 21/94; G01N 21/8806;
(Continued)

(56) References Cited

U.S. PATENT DOCUMENTS 6,539,106 B1  3/2003  Gallarda et al.
6,690,469 B1  2/2004  Shibata et al.
(Continued)

FOREIGN PATENT DOCUMENTS

JP  2001-208697  8/2001
JP  2002-221495  8/2002
(Continued)

OTHER PUBLICATIONS

U.S. Appl. No. 14/049,040, filed Oct. 8, 2013, Inoue, et al.
(Continued)

*Primary Examiner* — Farhan Mahmud
(74) *Attorney, Agent, or Firm* — Oblon, McClelland, Maier & Neustadt, L.L.P.

(57) ABSTRACT

An inspection apparatus comprising, an optical system emitting light having a predetermined wavelength, illuminating a sample while the light is converted into light having a polarization plane not in the range of −5 degrees to 5 degrees and 85 degrees to 95 degrees with respect to a direction of a repetitive pattern on the sample, an optical system for acquiring an image and forming said image on an image sensor using a lens, a half-wave plate, a first image sensor, a second image sensor, an inspection analyzer, wherein these differ in a transmission axis direction, a processor that obtains an average gray level and a standard deviation in each predetermined unit region of the image, and a defect detector, wherein a resolution limit defined by a wavelength of the light source and a numerical aperture of the lens is a value in which the pattern is not resolved.

9 Claims, 12 Drawing Sheets

(51) Int. Cl.
*G01N 21/95* (2006.01)
*B82Y 40/00* (2011.01)
*G01N 21/88* (2006.01)

(58) Field of Classification Search
CPC .... G01N 21/95623; G01N 21/21; G03F 1/84; G03F 7/70566; G06T 2207/30148; G06T 7/001; H01L 22/12
See application file for complete search history.

(56) References Cited

U.S. PATENT DOCUMENTS

| | | | |
|---|---|---|---|
| 2004/0028267 A1 | 2/2004 | Shoham et al. | |
| 2004/0125375 A1 | 7/2004 | Some | |
| 2004/0223141 A1* | 11/2004 | Rosengaus | G01N 21/9503 356/237.1 |
| 2006/0244976 A1* | 11/2006 | Baer | G03F 7/7065 356/600 |
| 2007/0002344 A1* | 1/2007 | Klassen | H04N 1/00002 358/1.9 |
| 2011/0249112 A1 | 10/2011 | Endo | |
| 2011/0255770 A1 | 10/2011 | Touya et al. | |
| 2012/0274931 A1* | 11/2012 | Otani | G01N 21/21 356/237.3 |
| 2013/0176559 A1 | 7/2013 | Ogawa et al. | |
| 2014/0002826 A1 | 1/2014 | Inoue et al. | |
| 2014/0043467 A1 | 2/2014 | Yamashita | |
| 2014/0055774 A1 | 2/2014 | Sugihara et al. | |
| 2014/0055780 A1 | 2/2014 | Ogawa et al. | |
| 2014/0072202 A1 | 3/2014 | Ogawa et al. | |
| 2014/0104412 A1 | 4/2014 | Inoue et al. | |
| 2014/0111636 A1 | 4/2014 | Inoue et al. | |
| 2014/0204202 A1 | 7/2014 | Ogawa et al. | |
| 2014/0232849 A1 | 8/2014 | Ogawa et al. | |

FOREIGN PATENT DOCUMENTS

| | | |
|---|---|---|
| JP | 2006-047308 A | 2/2006 |
| JP | 2006-512588 | 4/2006 |
| JP | 2007-225341 | 9/2007 |
| JP | 4236825 | 3/2009 |
| JP | 2009-192520 | 8/2009 |
| JP | 2012-127856 | 7/2012 |
| JP | 2012185178 | 9/2012 |
| JP | 2014-137358 | 7/2014 |
| WO | WO 2010/050448 | 5/2010 |

OTHER PUBLICATIONS

U.S. Appl. No. 14/059,847, filed Oct. 22, 2013, Inoue, et al.
U.S. Appl. No. 14/468,605, filed Aug. 26, 2014, Ogawa.
Japanese Office Action dated Sep. 6, 2016 in Application No. 2013-007793, with translation (8 pages).

* cited by examiner

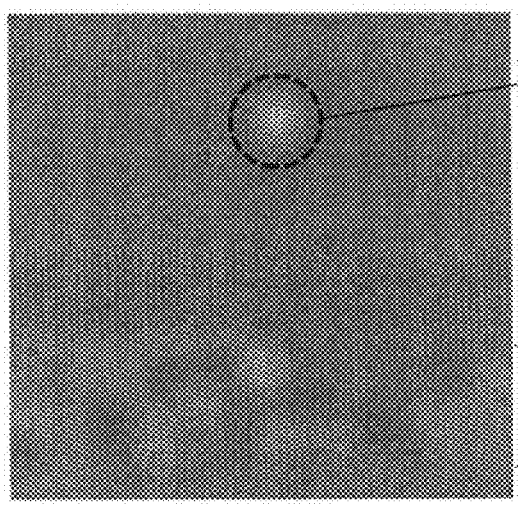
FIG. 5
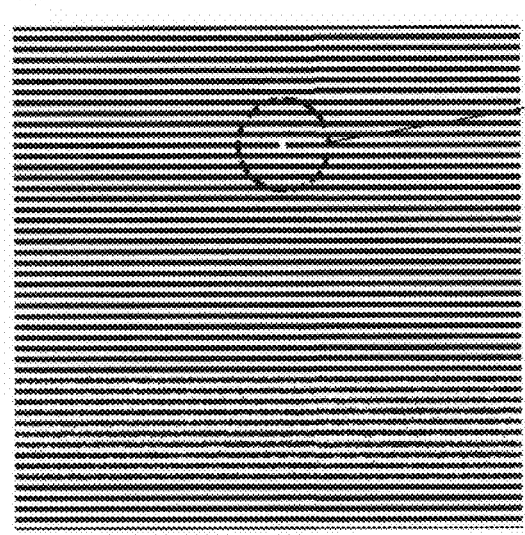
FIG. 4

INSPECTION APPARATUS

CROSS-REFERENCE TO THE RELATED APPLICATION

The entire disclosure of the Japanese Patent Application No. 2013-007793, filed on Jan. 18, 2013 including specification, claims, drawings, and summary, on which the Convention priority of the present application is based, are incorporated herein in its entirety.

FIELD OF THE INVENTION

The present invention relates to an Inspection Apparatus.

BACKGROUND

With high integration and large capacity of a Large Scale Integration (LSI), a circuit dimension required for a semiconductor element becomes increasingly narrow. Using an original image pattern (that is, a mask or a reticle, hereinafter collectively referred to as a mask), a reduced-projection exposure apparatus called a stepper or a scanner exposes and transfers the pattern on a wafer to form a circuit, thereby producing the semiconductor element.

It is necessary to improve a production yield for costly LSI production. At this point, a shape defect of the mask pattern can be cited as a large factor that degrades the production yield.

On the other hand, there is a demand for pattern formation having a line width of tens nanometers in a contemporary typical logic device. The shape defect of the mask pattern also becomes finer in such a situation. In order to absorb deviations of various LSI process conditions, it is necessary to enhance dimension accuracy of the mask and detect the defect of the extremely small pattern in mask inspection. Therefore, high accuracy is required for an apparatus that evaluates the pattern of a transfer mask used in the LSI production. For example, Japanese Patent No. 4236825 discloses an inspection apparatus that can detect the fine defect on the mask.

Recently, as a technique for forming a fine pattern, nanoimprint lithography (NIL) has attracted attention. In this technique, a template having a nanoscale microstructure is pressured on a specific resist formed on a wafer to form the fine circuit pattern on the resist.

In nanoimprint technology, in order to increase productivity, plural duplicate templates (replica templates) are produced using a master template, that is, of an original plate, and the replica templates are used while attached to different nanoimprint apparatuses. It is necessary to produce the replica template corresponding precisely to the master template. Therefore, it is necessary that not only the pattern of the master template but also the pattern of the replica template be evaluated with high accuracy.

Generally the mask is formed with a dimension four times the circuit dimension. The pattern is reduced and exposed onto a resist on the wafer by a reduced projection exposure device, using the photo-mask, and thereafter, the circuit pattern is developed. On the other hand, in the nanoimprint lithography, the template is formed with magnification equal to the circuit dimension. Therefore, the shape defect in the pattern of the template has the large influence on the pattern transferred onto the wafer compared with the shape defect in the pattern of the mask. Accordingly, it is necessary to evaluate the pattern of the template with higher accuracy compared with the case that pattern of the mask is evaluated.

Recently, with the progress of the fine circuit patterns, the pattern dimension is finer than a resolution of an optical system of a pattern evaluation apparatus. For example, when a line width of the pattern formed in the template is less than 50 nm, the pattern cannot be resolved by a light source of DUV (Deep UltraViolet radiation) light having a wavelength of about 190 nm to about 200 nm. The optical system is relatively easily constructed for the DUV light having the wavelength of about 190 nm to about 200 nm. Therefore, the light source of an EB (Electron Beam) is used. However, unfortunately the light source of the EB is not suitable for quantity production because of low throughput.

There is a demand for an inspection apparatus that can accurately inspect the fine pattern without generating the throughput degradation.

There are various types of defect in the pattern. Among others, a short-circuit defect which means that the lines short-circuit each other and an open-circuit defect which means that the line is disconnected have the largest influence on performance of the mask or template. FIG. 1 illustrates an example of the short-circuit defect. The two adjacent lines are connected to each other in a region A1 to generate the short-circuit defect. FIG. 2 illustrates an example of the open-circuit defect. The line is partially disconnected in a region A2.

On the other hand, the edge roughness as seen in a region A3 in FIG. 3 has a restrictive influence on the performance of the mask or template.

Even though all defects can be detected, that is, defects that may cause a problem and defects that will not cause a problem, the inspection can be efficiently performed when only the defect that may cause a problem to the mask or template is detected. However, the short-circuit defect, the open-circuit defect, and edge roughness (shown in the region A3 in FIG. 3) are less than or equal to a resolution limit. In the case that the short-circuit defect, the open-circuit defect, and the edge roughness are mixed in a repetitive pattern having a period of the resolution limit or less, brightness and darkness caused by the defect, such as the short-circuit defect and the open-circuit defect, which becomes a problem and brightness and darkness caused by the edge roughness are not distinguished from each other in observation with the optical system. The same holds true for a bright-field image and a dark-field image. This is because the short-circuit defect, the open-circuit defect, and the edge roughness are identical in size, namely, spread to the size of an extent of the resolution limit in an optical image.

FIG. 4 schematically illustrates a line and space pattern. In FIG. 4, it is assumed that the pattern dimension is smaller than the resolution limit of the optical system. In a region B1 of FIG. 4, the line pattern is partially lacks. In a region B2, the pattern edge roughness increases. The defects are clearly distinguished from each other on an actual substrate. However, the defects cannot be distinguished from each other when observed through the optical system. This is because the optical system acts as a spatial frequency filter that is defined by a wavelength λ of the light emitted from the light source and a numerical aperture NA. FIG. 5 illustrates an example in which the spatial frequency filter is applied to the pattern in FIG. 4. The defect in the region B1 and the defect in the region B2 are identical in size, and the difference of the shape is hardly recognized. Accordingly, the short-circuit defect which is less that the resolution limit is difficult to be distinguished with the defect caused by edge roughness which is also less than the resolution limit.

The present invention has been devised to solve the above problems. An object of the present invention is to provide an inspection apparatus that can accurately inspect the fine pattern without generating the throughput degradation, more particularly an inspection apparatus that can distinguish the defect to be detected from a defect that is not to be detected.

SUMMARY OF THE INVENTION

According to one aspect of the present invention, an inspection apparatus comprising, an illumination optical system that includes a light source emitting light having a predetermined wavelength, and illuminates a sample, that is an inspection target, with the light emitted from the light source that is linearly-polarized light having a polarization plane of an angle except in the range of −5 degrees to 5 degrees and 85 degrees to 95 degrees with respect to a repetitive direction of a repetitive pattern on the sample, an imaging optical system that includes an inspection image sensor for acquiring an optical image of the pattern formed on the sample, and forms an image of the light reflected by or transmitted through the sample on the inspection image sensor using a lens, a half-wave plate that transmits the light reflected by or transmitted through the sample, a splitter unit that splits the light, in which a polarization direction is rotated by the half-wave plate, into three directions, a first measuring image sensor to which the light split into a first direction by the splitter unit is incident through a first measuring analyzer, a second measuring image sensor to which the light split into a second direction by the splitter unit is incident through a second measuring analyzer, an inspection analyzer that is disposed on an optical path to the inspection image sensor, the optical path being a third direction into which the light is split by the splitter unit, wherein the first measuring analyzer, the second measuring analyzer, and the inspection analyzer differ from one another in a transmission axis direction, and the transmission axis direction of the inspection analyzer is located between the transmission axis direction of the first measuring analyzer and the transmission axis direction of the second measuring analyzer, an image processor that obtains an average gray level and a standard deviation in each predetermined unit region of the optical image, and a defect detector that detects a defect of the sample, wherein a resolution limit defined by a wavelength of the light source and a numerical aperture of the lens is a value in which the pattern is not resolved.

Further to this aspect of the present invention, the inspection apparatus, further comprising an angle controller that controls an angle of the half-wave plate, wherein the image processor acquires a first measurement signal ($\sigma/\sqrt{A}$) from a standard deviation ($\sigma$) of a gray level and an average gray level (A) with respect to the optical image acquired by the first measuring image sensor, and acquires a second measurement signal ($\sigma/\sqrt{A}$) from the standard deviation ($\sigma$) of the gray level and the average gray level (A) with respect to the optical image acquired by the second measuring image sensor, calculates a polarization characteristic signal defined by an formula (1), $$\{(\text{first measurement signal})-(\text{second measurement signal})\}/\{(\text{first measurement signal})+(\text{second measurement signal})\} \quad \text{formula (1):}$$

rotates the half-wave plate before inspection, obtains a value of the polarization characteristic signal when the measurement signal ($\sigma/\sqrt{A}$) becomes a minimum in the optical image acquired by the inspection image sensor, sets the value to a desired value, and transmits the desired value to the angle controller, and the angle controller controls the angle of the half-wave plate such that the polarization characteristic signal defined by the formula (1) becomes the desired value.

Further to this aspect of the present invention, the inspection apparatus, wherein the half-wave plate has a structure in which the angle thereof can arbitrarily be adjusted by a rotation system, and the angle controller controls the rotation system.

Further to this aspect of the present invention, the inspection apparatus, wherein the splitter unit includes a first beam splitter and a second beam splitter, the light reflected by the first beam splitter is incident to the first measuring image sensor through the first measuring analyzer, the light, which is transmitted through the first beam splitter and reflected by the second beam splitter, is incident to the second measuring image sensor through the second measuring analyzer, and the light transmitted through the first beam splitter and the second beam splitter is incident to the inspection image sensor through the inspection analyzer.

Further to this aspect of the present invention, the inspection apparatus, wherein the light source emits deep ultraviolet radiation light.

Further to this aspect of the present invention, the inspection apparatus, further comprising a comparison unit that compares the optical image acquired by the inspection image sensor to a standard image, and determines that a defect exists when a difference value between the optical image and the standard image exceeds a predetermined threshold.

Further to this aspect of the present invention, the inspection apparatus, further comprising a reference image producing unit that produces a reference image, wherein the standard image is the reference image that is produced from design data of the pattern, and the reference image produced by the reference image producing unit is transmitted to the comparison unit.

BRIEF DESCRIPTION OF THE DRAWINGS

FIG. 4 schematically illustrates a line and space pattern.

FIG. 5 illustrates an example in which the spatial frequency filter is applied to the pattern in FIG. 4.

DETAILED DESCRIPTION OF THE EMBODIMENTS

Figure 3:
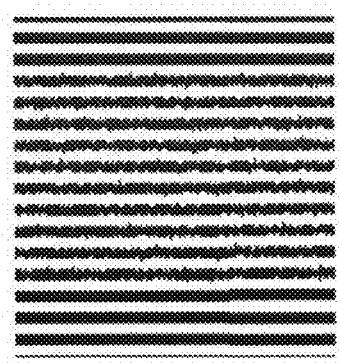
FIG. 3 illustrates an example of a defect caused by edge roughness.

Many patterns formed on a semiconductor wafer are repetitive patterns such as a line and space pattern, namely, regularly repeating patterns having periodicity. Therefore, the repetitive pattern is also used in a master pattern and a daughter pattern in the nanoimprint lithography.

In the case that an image of the pattern in which a line width is less than 50 nm is formed with an optical system in which DUV (Deep UltraViolet radiation) light is used, even if a theoretical-limitation lens (numerical aperture NA=1) is used, the pattern can be resolved only by liquid immersion. However, in the case that the pattern is the repetitive pattern, regularity is disturbed to change a gray level of an optical image near a defect when edge roughness increases in a part of the pattern, or when the pattern is partially lacking. Accordingly, a short-circuit defect, an open-circuit defect, and the defect caused by the edge roughness can be detected by comparing the gray levels of elements. The change in gray level will be described in detail below.

When being acquired with the optical system, an image of fine irregularity (hereinafter referred to as roughness) of a pattern edge located within a range of a dimension corresponding to a resolution limit of the optical system becomes a dull shape having the dimension of almost the resolution limit of the optical system without resolving an individual irregularity shape. Because an amplitude and a frequency of the edge roughness are random, the pattern regularity is disturbed, and the image of the edge roughness is acquired as bright and dark unevenness over a whole range of a sample.

In the case that the pattern is partially lacking, similarly, the image of the fine irregularity is magnified to a size of almost the resolution limit of the optical system. That is, because the regularity is disturbed by the lack of the pattern although the pattern is not resolved, a region near the defect has the gray level different from an average gray level of a surrounding region. The same holds true for the case that the pattern is partially connected to the adjacent pattern.

Thus, the defect can be detected by checking the change in gray level, even if the repetitive pattern has a period that is less than or equal to the resolution of the optical system. However, as described above, the detected defects having the resolution limit or less, namely, the short-circuit defect or open-circuit defect and the bright and dark unevenness caused by the edge roughness are difficult to distinguished from each other.

The inventor has devised the present invention by paying attention to the fact that the large defects such as the short-circuit defect and the open-circuit defect have a large influence on a polarization state of illumination light compared with the small defects such as the defect caused by the edge roughness. According to the present invention, by controlling the polarization state of the illumination light and a condition of a polarization control element of the optical system forming the image of the light reflected from a substrate that becomes an inspection target, the bright and dark unevenness caused by the edge roughness can be removed with the polarization control element to extract only a change in amplitude of the short-circuit defect or open-circuit defect.

Figure 2:
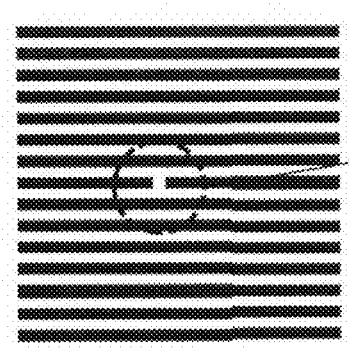
FIG. 2 illustrates an example of the open-circuit defect.
Figure 1:
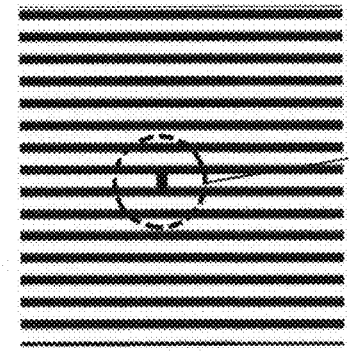
FIG. 1 illustrates an example of the short-circuit defect.

For example, for the short-circuit defect in FIG. 1, sensitivity for an electric field component of the illumination light varies between vertical and horizontal directions by connection of lines adjacent to each other. For example, when linearly-polarized light perpendicularly incident to a substrate has a polarization direction of 45 degrees with respect to a direction of a line and space edge, while a vertical component and a horizontal component of the electric field of the incident light are equal to each other, the horizontal component of the electric field of the reflected light is larger than the vertical component due to the short-circuit defect. As a result, the polarization direction of the light reflected from the short-circuit defect is inclined in the direction orthogonal to the direction of the line and space edge. For the open-circuit defect as seen in FIG. 2, the polarization direction is inclined in the direction of the line and space edge.

On the other hand, the defect caused by the edge roughness in FIG. 3 is not the defect caused by lines connected to each other or the defect caused by the line being disconnected. Because an irregularity size in the edge roughness, even if identified as a defect, is finer than the short-circuit defect and the open-circuit defect, there is a small difference in sensitivity between the vertical and horizontal directions of the electric field component of the illumination light. Accordingly, for example, when the linearly-polarized light perpendicularly incident to the substrate has the polarization direction of 45 degrees with respect to the direction of the line and space edge, the polarization direction of the light scattered by the edge roughness becomes a value close to 45 degrees that is of the polarization direction of the incident light. However, because the polarization direction is influenced by a base pattern having the periodic repetition, the polarization direction does not completely become 45 degrees, but the polarization direction has the value slightly deviated from 45 degrees.

The defect can be classified by taking advantage of the difference of the influence exerted on the polarization state of the illumination light. Specifically, the classification of the defect can be performed using the optical system in FIG. 6.

Figure 6:
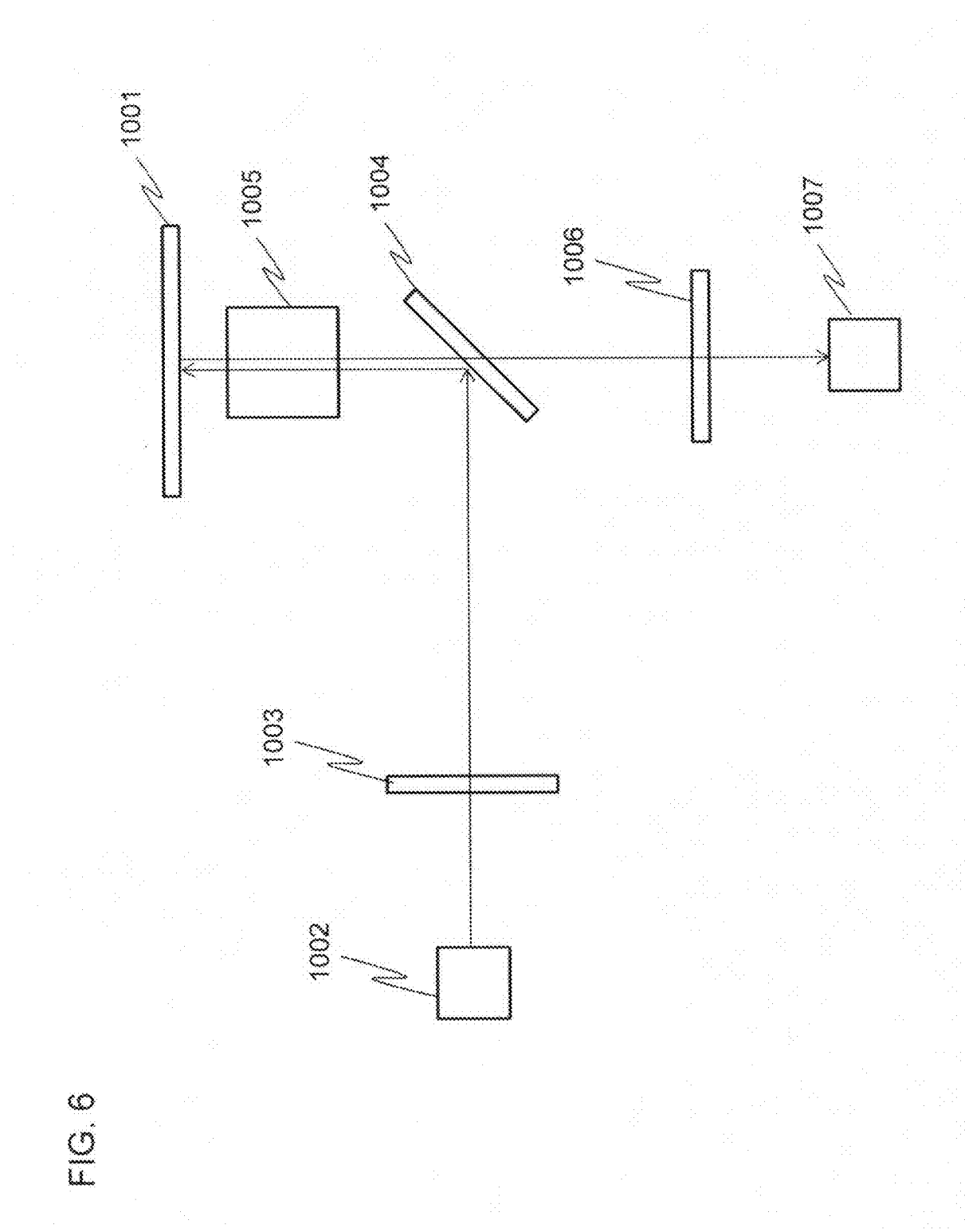
FIG. 6 illustrates an optical system according to the present embodiment.

In FIG. 6, it is assumed that the light with which a mask 1001, that is, the inspection target is illuminated is the linearly-polarized light having a polarization plane of 45 degrees with respect to a periodic direction of a periodic pattern formed on the mask. Therefore, the difference in sensitivity between the large defect such as the short-circuit defect and the open-circuit defect and the small defect such as the defect caused by the edge roughness can emerge with respect to the electric field component of the illumination light. When the illumination light has the polarization plane of 0 degree or 90 degrees with respect to the periodic direction of the periodic pattern formed on the mask, the sensitivity of the illumination light becomes even between the defects, and the large defect and the small defect cannot be distinguished from each other. Therefore, it is necessary that the polarization plane be not 0 degree or 90 degrees with respect to the periodic direction of the periodic pattern. However, the polarization plane is not necessarily 45 degrees. Preferably the polarization plane is set to the angle except ranges of −5 degrees to 5 degrees and 85 degrees to 95 degrees.

Referring to FIG. 6, the light, which is emitted from a light source 1002 and transmitted through a half-wave plate 1003, is reflected by an unpolarized beam splitter 1004 to illuminate the mask 1001 through an objective lens 1005. The light reflected by the mask 1001 is incident to an image sensor 1007 after transmitted through the objective lens 1005, the unpolarized beam splitter 1004, and an analyzer 1006. Therefore, an optical image of the pattern formed on the mask 1001 is obtained.

As illustrated in FIG. 6, the analyzer 1006 is disposed in the imaging optical system, which allows only the light in the specific polarization direction to be extracted. Specifically, the incidence of the scattering light to the image sensor 1007 from the defect can almost completely be prevented by setting the direction of the analyzer 1006 to the direction orthogonal to the polarization direction of the light scattered by the edge roughness. On the other hand, the light scattered by the short-circuit defect and the open-circuit defect is transmitted through the analyzer 1006, and is incident to the image sensor 1007 because the polarization direction is inclined. Accordingly, the optical image in which the short-circuit defect and the open-circuit defect remain while the bright and dark unevenness caused by the edge roughness is removed can be obtained.

FIG. 6 illustrates an example of a bright-field illumination system. However, even in a dark-field illumination system or a transmission illumination system, the optical image in which the bright and dark unevenness caused by the edge roughness is removed can be obtained by taking advantage of the polarization.

A specific method for finding a condition that excludes the bright and dark unevenness caused by the edge roughness will be described below. As described above, the defect caused by the edge roughness can be removed from the optical image using the optical system in FIG. 6. For this reason, it is necessary to control the polarization state of the illumination light and the condition of the polarization control element of the optical system forming the image of the light reflected from the inspection target.

Generally, in the mask or template that becomes the inspection target, many pieces of edge roughness exist over the whole surface while few short-circuit defects or open-circuit defects exist. For example, when the optical image having the region of 100 μm×100 μm is acquired, there is only a small possibility that the short-circuit defect or the open-circuit defect is included in the region, and there are few defects even if the short-circuit defect or the open-circuit defect is included in the region. That is, the brightness and darkness of the optical image in the region is substantially caused by the edge roughness. This means that the condition that removes the defect caused by the edge roughness is obtained by one optical image having the dimension of about 100 μm×about 100 μm.

The change in gray level caused by the edge roughness in the optical image can be removed by controlling the polarization direction of the light incident to the image sensor on the imaging optical system side. Specifically, by controlling the direction of the analyzer in the imaging optical system, a quantity of scattering light that is incident to the image sensor due to the edge roughness can be changed to vary the bright and dark amplitude in the optical image.

The bright and dark amplitude in the optical image can be expressed by a standard deviation of the gray level in each pixel. For example, when the optical system has a pixel resolving power of 50 nm, the optical image having the region of 100 μm×100 μm is expressed by 4 million pixels. That is, a specimen of 4 million gray levels is obtained from the one optical image.

For the dark-field illumination system, the standard deviation is obtained with respect to the sample, the obtained value is defined as an extent of the scattering light caused by the edge roughness, and the polarization state on the imaging optical system side, for example, the angle of the analyzer 1006 in FIG. 6 is adjusted such that the value becomes the minimum. Alternatively, the half-wave plate is disposed in an optical path of the imaging optical system, and the angle of the half-wave plate may be adjusted. Therefore, the quantity of scattering light incident to the image sensor due to the edge roughness can be minimized.

On the other hand, for the optical image in the bright-field optical system, the extent of the brightness and darkness caused by the edge roughness is influenced by zero-order light. The reason is as follows. Because the fine periodic pattern that is less than or equal to the resolution limit exists in the inspection target, the polarization state of the zero-order light changes due to a phase-difference effect caused by structural birefringence. Therefore, the light quantity that becomes a base also changes when the analyzer or the half-wave plate is rotated in order to remove the reflected light caused by the edge roughness. Because the bright-field image is a product of the electric field amplitude of the scattering light from the short-circuit defect, the open-circuit defect, or the edge roughness and the electric field amplitude of the zero-order light, the extent of the brightness and darkness caused by the edge roughness is influenced by an intensity of the zero-order light as described above.

Figure 7:
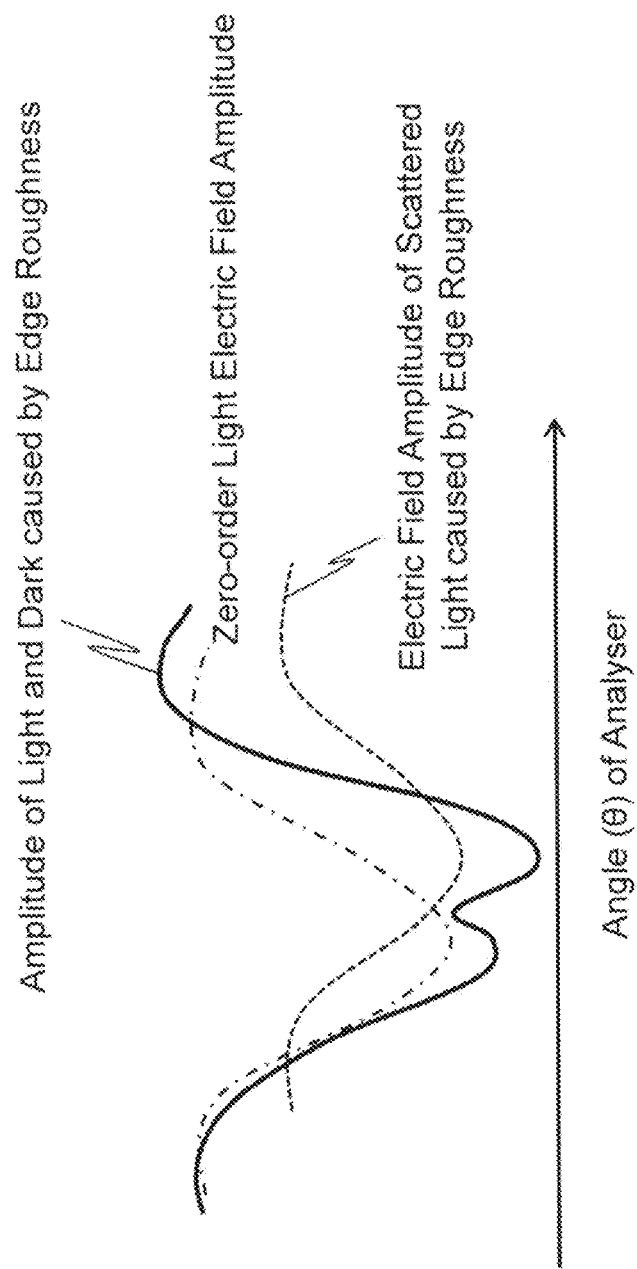
FIG. 7 illustrates angle dependence on the analyzer with respect to the amplitude of the brightness and darkness caused by the edge roughness, the electric field amplitude of the scattering light, and the electric field amplitude of the zero-order light.

FIG. 7 illustrates angle dependence on the analyzer with respect to the amplitude of the brightness and darkness caused by the edge roughness, the electric field amplitude of the scattering light, and the electric field amplitude of the zero-order light. In the bright-field optical system, when the polarization state of the scattering light caused by the edge roughness is not matched with the polarization state of the zero-order light influenced by the structural birefringence, the angle dependence that is the product of both on the analyzer with respect to the amplitude of the brightness and darkness caused by the edge roughness has two local minima as illustrated in FIG. 7.

The reason the amplitude of the brightness and darkness caused by the edge roughness is expressed by the product of the electric field amplitude of the scattering light from the defect caused by the edge roughness and the electric field amplitude of the zero-order light will be described below.

It is assumed that the electric field amplitude of the zero-order light is put as follows.

$$E_0 = f(\theta)$$

The electric field amplitude of the scattering light caused by the edge roughness is put as follows.

$$E_r = g(\theta)$$

The zero-order light becomes elliptically-polarized light having a long axis in a predetermined direction by the influence of the birefringence caused by the fine pattern. Therefore, $f(\theta)$ has one local maximum in the range θ of 0 degree to 180 degrees, and becomes a function having the local minimum greater than 0. On the other hand, in the scattering light caused by the edge roughness, because the roughness does not have the periodicity, the phase difference is small if any, and the linear polarization is substantially maintained. Therefore, $g(\theta)$ has one local minimum in the range θ of 0 degree to 180 degrees, and becomes a function having the local minimum close to 0.

As indicated by the following equation, a signal intensity I of the bright-field image is expressed by interference between the electric field of the zero-order light and the electric field of the scattering light caused by the edge roughness.

$$I=<|E_0\exp\{i(\omega t)\}+E_r\exp\{i(\omega t+\phi)\}|>=E_0^2+E_r^2+2E_0E_r\cos(\phi)$$

In the above equation, because $E_0^2$ is a square of the zero-order light, namely, a base light quantity $I_0$, an amplitude $I_r$ of the brightness and darkness caused by the edge roughness is expressed by the following equation.

$$I_r=I-I_0=E_r^2+2E_0E_r\cos(\phi)$$

Where $\phi$ is the phase difference between the zero-order light and the scattering light, and depends on a focal position of the substrate. For example, the following equation is considered as the condition that the brightness and darkness caused by the edge roughness become the strongest.

$$\cos(\phi)=1$$

While the edge roughness is extremely fine, as described above with reference to FIG. 7, the electric field amplitude of the zero-order light does not become zero due to the influence of the birefringence even if the angle θ of the analyzer is changed and thus, is approximated as follows.

$$E_r<<E_0$$

Accordingly, the amplitude of the brightness and darkness caused by the edge roughness can be simplified as expressed by the following equation.

$$I_r=2E_0E_r$$

Therefore, in the periodic pattern that is less than or equal to the resolution limit, the amplitude of the brightness and darkness caused by the edge roughness is expressed by the product of the electric field amplitude of the zero-order light and the electric field amplitude of the scattering light caused by the edge roughness.

As described above, because the $E_0$ and $E_r$ depend on the angle θ of the analyzer, $I_r$ is expressed by the following equation.

$$I_r=2f(\theta)g(\theta)$$

Accordingly, in the case that the value of the angle θ at which the function f(θ) becomes the minimum differs from the value of the angle θ at which the function g(θ) becomes the minimum, $I_r$ that is of the product of f(θ) and g(θ) has the two local minima.

In order that the influence of the scattering light caused by the edge roughness is removed to improve sensitivity for detecting the short-circuit defect or the open-circuit defect, it is necessary to find not the condition that the function f(θ) caused by the zero-order light becomes the minimum but the condition that the function g(θ) caused by the edge roughness becomes the minimum. This is because the minimum of the function f(θ) is only the condition that the base light quantity becomes the minimum and the influence of the edge roughness is hardly removed.

The condition that the function f(θ) becomes the minimum is obtained by a calculation using a standard deviation σ of the gray level of the optical image and an average gray level A. The standard deviation a includes various noise factors, and particularly the standard deviation σ is largely influenced by the brightness and darkness caused by the edge roughness. Therefore, the standard deviation σ can be regarded as the following equation.

$$\sigma \propto I_r=2f(\theta)g(\theta)$$

Because the average gray level A of the optical image is the base light quantity, namely, the intensity of the zero-order light, the average gray level A is expressed as follows.

$$A \propto I_0=E_0^2=f(\theta)^2$$

Accordingly, the function g(θ) is obtained by the following equation.

$$g(\theta) \propto \sigma/f(\theta)=\sigma/\sqrt{A}$$

Thus, the electric field amplitude of the scattering light caused by the edge roughness is proportional to a value in which the standard deviation σ of the optical image is divided by a square root of the average gray level A. In order to find the condition that minimizes the amplitude of the brightness and darkness caused by the edge roughness, the optical image is acquired while the angle θ of the analyzer is varied, and the value in which the standard deviation of the gray level in the acquired optical image is divided by the square root of the average gray level. Then the angle θ is obtained such that the value becomes the minimum.

Figure 8:
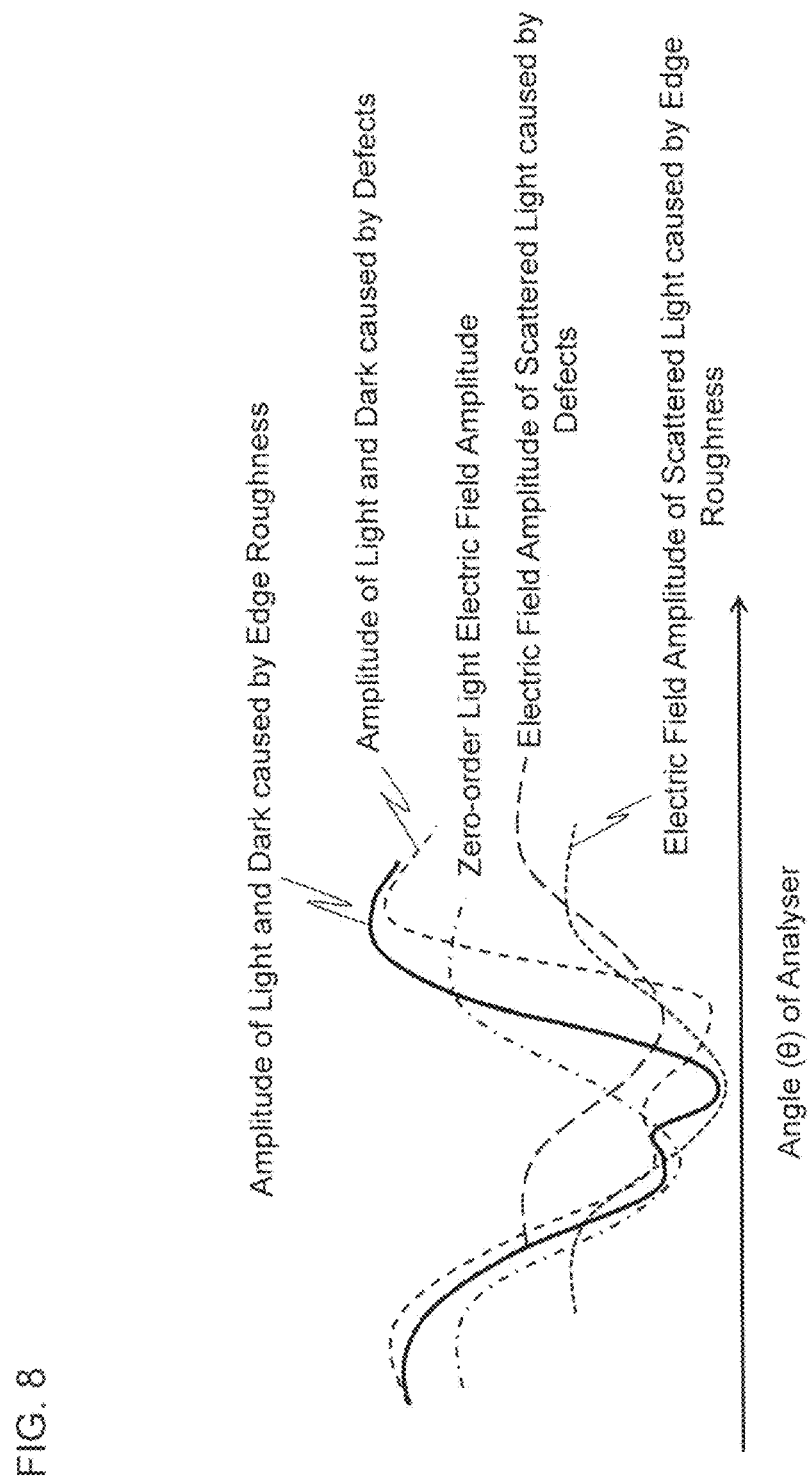
FIG. 8 illustrates the amplitude of the brightness and darkness caused by the short-circuit defect or the open-circuit defect and the electric field amplitude of the scattering light added to FIG. 7.

FIG. 8 illustrates the angle dependence on the analyzer, in which the amplitude of the brightness and darkness caused by the short-circuit defect or the open-circuit defect and the electric field amplitude of the scattering light are added to that of FIG. 7. As described above, in the large defect such as the short-circuit defect and the open-circuit defect, the vertical direction and the horizontal direction differ from each other in the sensitivity with respect to the electric field component of the illumination light. Accordingly, when the electric field amplitude of the scattering light caused by the large defect becomes the minimum, the angle θ of the analyzer differs from that of the scattering light caused by the edge roughness. That is, even if the angle θ is applied when the electric field amplitude of the scattering light caused by the edge roughness becomes the minimum, the electric field amplitude of the reflected light caused by the short-circuit defect or the open-circuit defect does not become the minimum. Therefore, the short-circuit defect and the open-circuit defect can be detected without being buried in the amplitude of the brightness and darkness caused by the edge roughness.

When the electric field amplitude of the scattering light caused by the edge roughness becomes the minimum, the value of the angle θ depends on a structure of the pattern formed in the inspection target. For example, the value of the angle θ at which the electric field amplitude becomes the minimum also changes when a pitch, a depth, or a line and space ratio of the pattern changes. Accordingly, it is necessary to obtain the angle θ according to the structure of the pattern that is of the inspection target. In the case that the identical pattern is provided in the inspection target, the obtained angle θ can continuously be used in an inspection process. However, in the case that plural patterns having different structures are provided in the inspection target, the angle θ is changed according to the pattern. Additionally, even in the identical design pattern, the depth or the line and space ratio is slightly changed by various error factors, and possibly the angle θ of the analyzer, which minimizes the electric field amplitude of the scattering light, has a variation on the inspection target. Therefore, it is necessary to follow the variation. More particularly, the angle θ of the analyzer is also changed according to the change of the kind of the pattern to be inspected.

Preferably feedback control is used in order to correct a disturbance such as the variation in angle θ generated by the pattern change in real time. As described above, in order to minimize the amplitude Ir of the brightness and darkness caused by the edge roughness, it is necessary that the electric field amplitude Er of the scattering light caused by the edge roughness always take the local minimum. At this point, it is difficult that the electric field amplitude Er is kept at the minimum only by information on an inspection image while the inspection is performed. This is attributed to the following facts. That is, the local minimum of the electric field amplitude Er is obtained by reciprocating the angle θ of the analyzer at high speed between ranges across the local minimum of the electric field amplitude from each other, and it is necessary to control a median of the reciprocating motion of the angle θ such that the electric field amplitude Er is always located near the local minimum. In the method, because the influence cannot be removed when the electric field amplitude Er deviated from the local minimum, degradation of inspection performance cannot be avoided. Therefore, the optical system that can obtain an optimum value of the angle θ at high speed will be described below.

Figure 9:
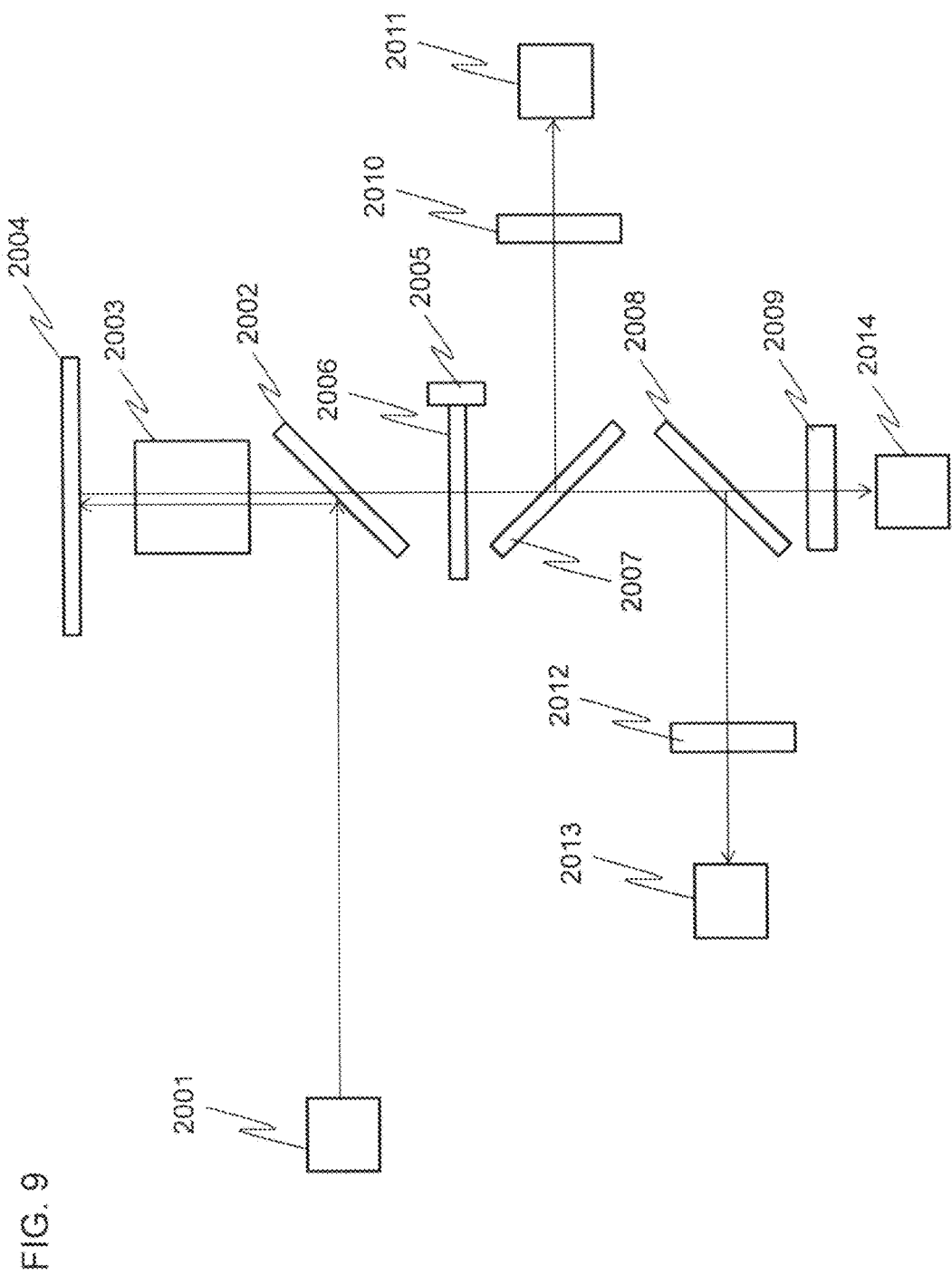
FIG. 9 illustrates a configuration of an inspection optical system according to the present embodiment.

FIG. 9 is a view illustrating a configuration of an inspection optical system according to an embodiment. Referring to FIG. 9, a substrate 2004 that becomes the inspection target is illuminated with the light, which is emitted from a light source 2001 and reflected by a half mirror 2002, through an objective lens 2003. Then, the light reflected by the substrate 2004 is incident to the imaging optical system after transmitted through the objective lens 2003 and the half mirror 2002.

It is assumed that the light with which the substrate 2004 is illuminated is the linearly-polarized light having the polarization plane near 45 degrees or 135 degrees with respect to the repetitive direction of the periodic pattern formed on the substrate 2004. For example, this can be implemented by providing the half-wave plate (not illustrated) between the light source 2001 and the half mirror 2002. Therefore, the difference in sensitivity between the large defect such as the short-circuit defect and the open-circuit defect and the small defect such as the defect caused by the edge roughness can emerge with respect to the electric field component of the illumination light.

In FIG. 9, a half-wave plate 2006 including a rotation system 2005 is disposed in the imaging optical system. The light transmitted through the half mirror 2002 is transmitted through the half-wave plate 2006. At this point, the polarization direction of the light rotates by a predetermined angle. At this point, it is assumed that θ' is the angle of the polarized light rotated by the half-wave plate 2006.

A first beam splitter 2007, a second beam splitter 2008, and an inspection analyzer 2009 are disposed in this order in front of the half-wave plate 2006. The first beam splitter 2007 and the second beam splitter 2008 are the splitter units that split the light used to measure the electric field amplitude of the scattering light caused by the edge roughness.

The light reflected by the first beam splitter 2007 is transmitted through a first measuring analyzer 2010, and is incident to a first measuring image sensor 2011. On the other hand, part of the light transmitted through the first beam splitter 2007 is reflected by the second beam splitter 2008, transmitted through a second measuring analyzer 2012, and is incident to a second measuring image sensor 2013. The light transmitted through the second beam splitter 2008 is transmitted through the inspection analyzer 2009, and is incident to an inspection image sensor 2014.

Figure 15:
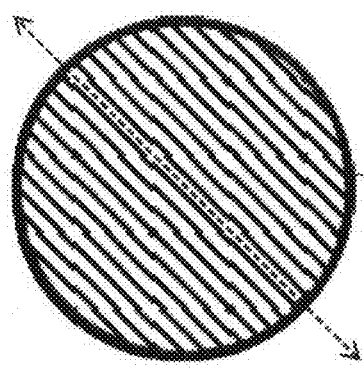
FIG. 15 illustrates the inspection analyzer.
Figure 16:
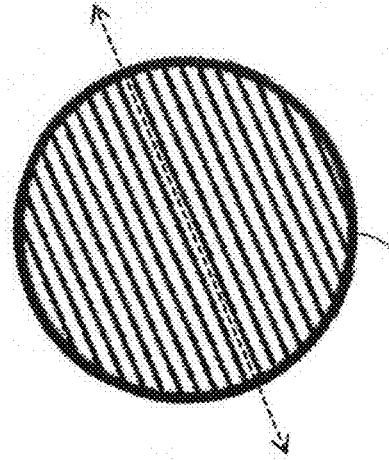
FIG. 16 illustrates the first measuring analyzer.
Figure 17:
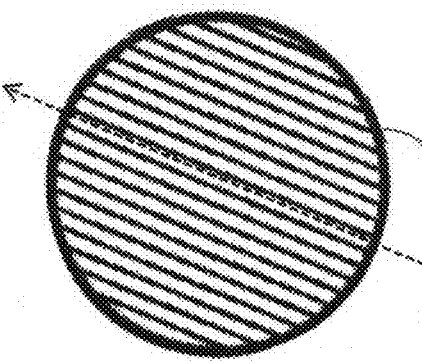
FIG. 17 illustrates the second measuring analyzer.

FIGS. 15, 16, and 17 are schematic sectional views of the inspection analyzer 2009, the first measuring analyzer 2010, and the second measuring analyzer 2012, respectively. An arrow in FIGS. 15, 16, and 17 indicates the direction of each transmission axis.

As can be seen from FIGS. 15 to 17, the directions of the transmission axes differ from each other. The transmission axis direction of the inspection analyzer 2009 is located between the transmission axis direction of the first measuring analyzer 2010 and the transmission axis direction of the second measuring analyzer 2012. Therefore, the quantity of scattering light, which is caused by the edge roughness and transmitted through the half-wave plate 2006 having the angle θ, can be changed between the image acquiring elements. The change in quantity of the scattering light incident to the inspection analyzer 2009 is interpolated between the change in quantity of the scattering light incident to the first measuring image sensor 2011 and the change in quantity of the scattering light incident to the second measuring image sensor 2013, so that the change in quantity of the scattering light incident to the inspection analyzer 2009 can be correctly obtained.

Figure 10:
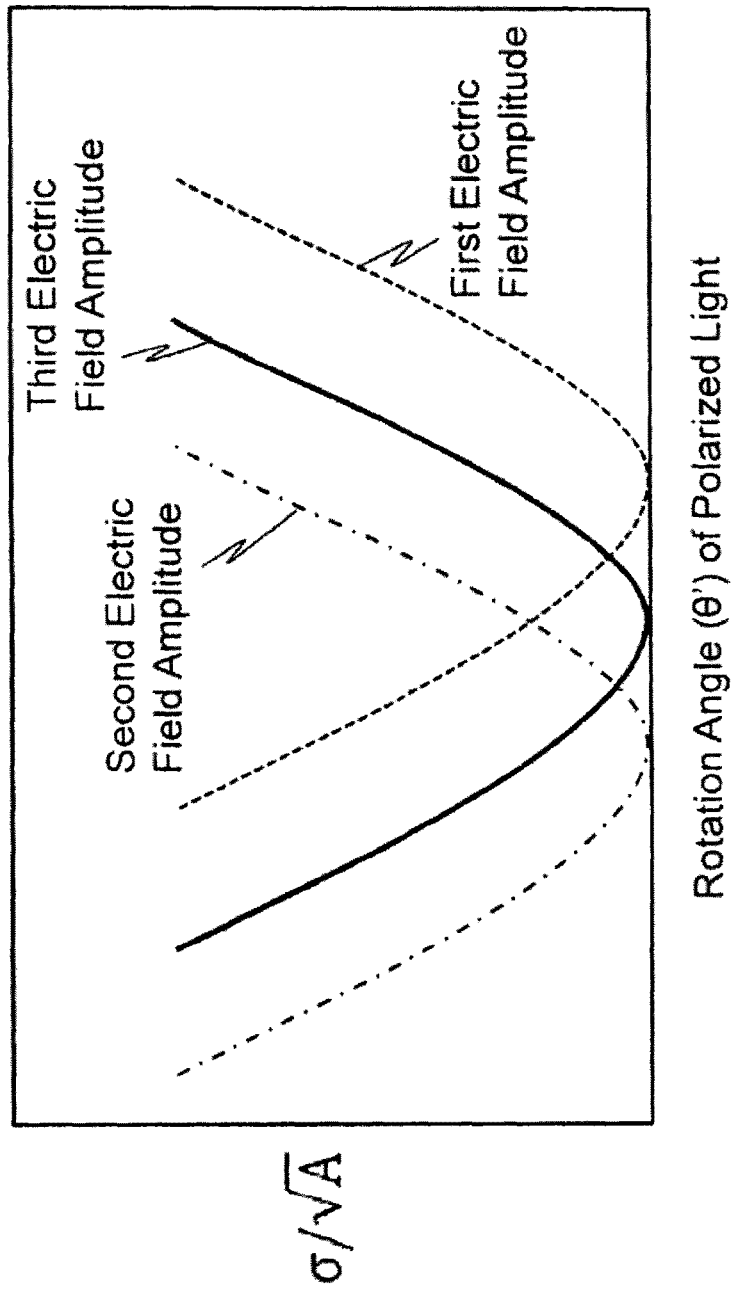
FIG. 10 illustrates the relationship of the electric field of scattering light between the rotating angle of each optical image acquired in the optical system of FIG. 9.

The standard deviation σ of the gray level and the average gray level A are obtained with respect to each of the optical images acquired by the first measuring image sensor 2011, the second measuring image sensor 2013, and the inspection image sensor 2014. Because the electric field amplitude of the scattering light caused by the edge roughness is proportional to the value ($\sigma/\sqrt{A}$) in which the standard deviation σ of the gray level is divided by the square root of the average gray level A of the optical image, a relationship between the electric field amplitude of the scattering light in each optical image and the rotation angle is obtained when the obtained value is plotted with respect to the rotation angle (θ') of the polarized light. FIG. 10 illustrates an example.

FIG. 10 illustrates the relationship of the electric field of scattering light between the rotating angle of each optical image acquired in the optical system of FIG. 9. In particular, FIG. 10 illustrates:

The First Electric Field Amplitude: Electric Field Amplitude of Scattered Light caused by Edge Roughness in an Optical Image acquired by the First Measurement image Sensor.

The Second Electric Field Amplitude: Electric Field Amplitude of Scattered Light caused by Edge Roughness in an Optical Image acquired by the Second Measurement image Sensor.

The Third Electric Field Amplitude: Electric Field Amplitude of Scattered Light caused by Edge Roughness in an Optical Image acquired by the Inspection Image Sensor.

It is assumed that the value ($\sigma/\sqrt{A}$) obtained from the optical image acquired by the first measuring image sensor 2011 is a first measurement signal, and that the value ($\sigma/\sqrt{A}$) obtained from the optical image acquired by the second measuring image sensor 2013 is a second measurement signal. The value obtained by the following formula is defined as the polarization characteristic signal of the scattering light caused by the edge roughness.

{(first measurement signal)−(second measurement signal)}/{(first measurement signal)+(second measurement signal)}

Figure 11:
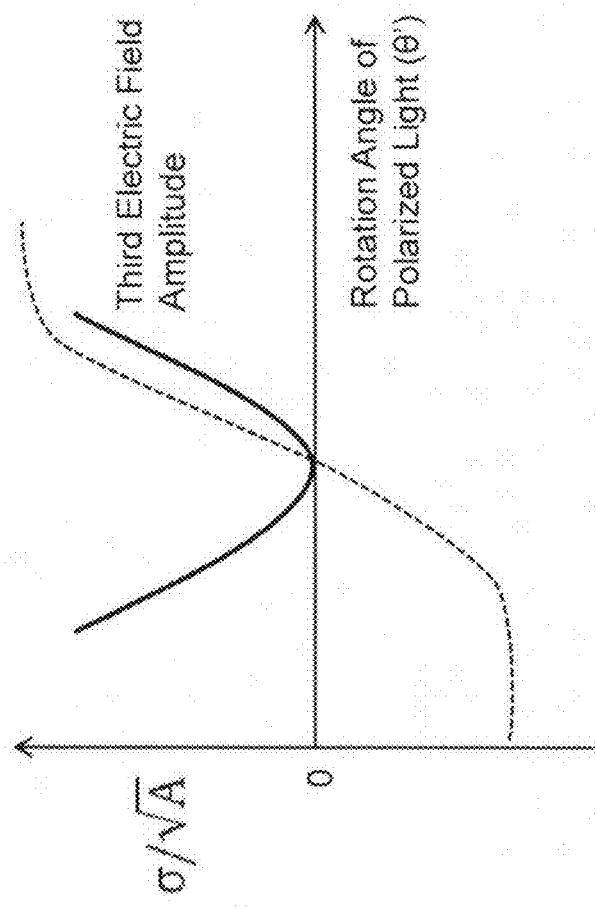
FIG. 11 illustrates an example in which a polarization characteristic signal of the scattering light obtained from the value ($\sigma/\sqrt{A}$) in each electric field amplitude illustrated in FIG. 10 and caused by the edge roughness, is plotted with respect to the rotation angle ($\theta$) of the polarized light.

FIG. 11 illustrates an example in which the value obtained from the value ($\sigma/\sqrt{A}$) in each electric field amplitude in FIG. 10 using the above formula is plotted with respect to the rotation angle (θ') of the polarized light. As can be seen from the example in FIG. 11, when the electric field amplitude of the scattering light, which is caused by the edge roughness and transmitted through the inspection analyzer 2009, becomes the local minimum, the polarization characteristic signal becomes the value around zero and has a substantially constant gradient around zero. Accordingly, the polarization characteristic signal can be maintained at a predetermined value around zero by the general feedback control.

Figure 12:
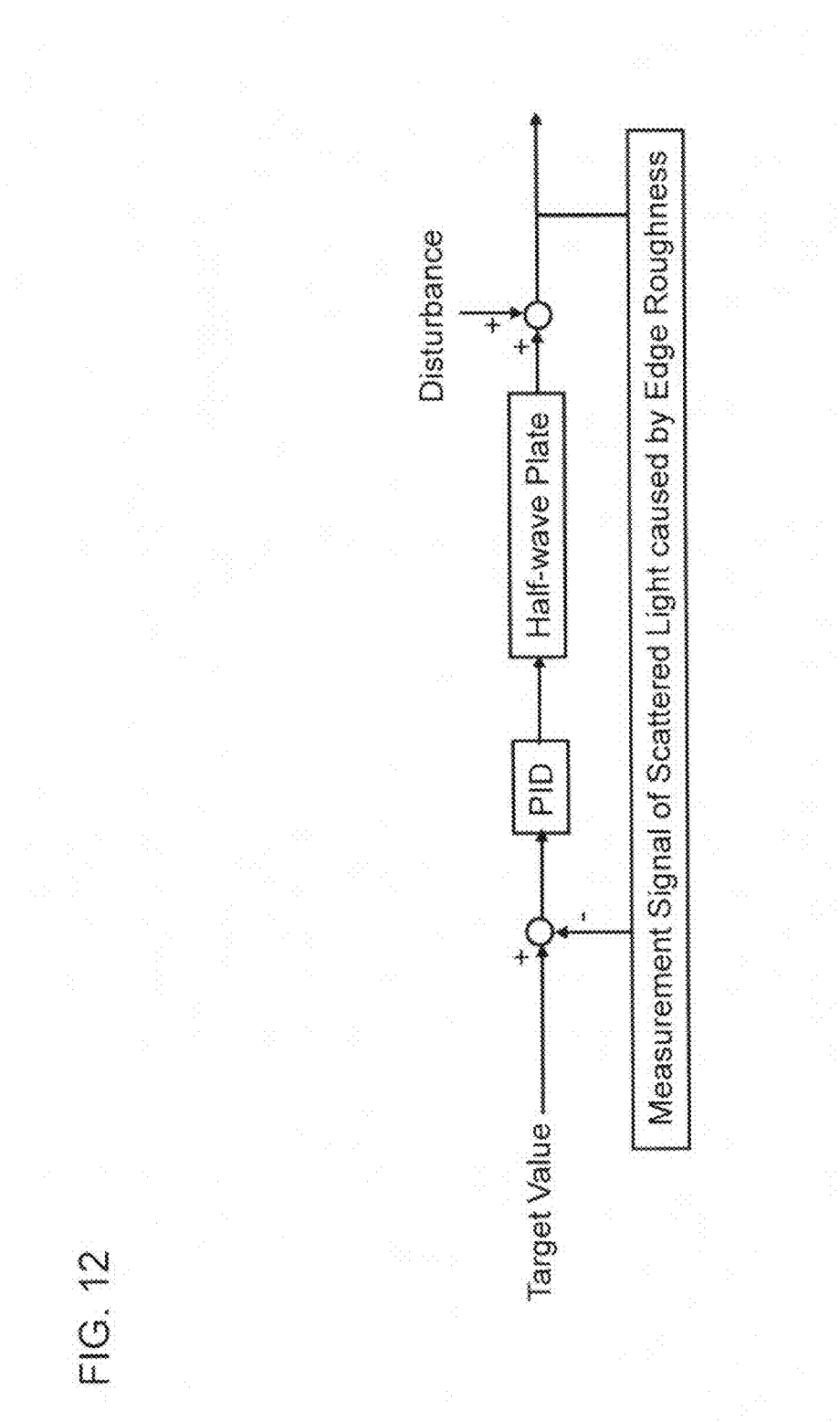
FIG. 12 illustrates an example of a feedback control system according to the embodiment.

FIG. 12 illustrates an example of a feedback control system of the embodiment. PID control is adopted in the example in FIG. 12. As used herein, the disturbance means a deviation in optimum angle of the half-wave plate, which is generated by the difference of the pattern structure provided in the substrate that is of an evaluation target, specifically a deviation in angle that minimizes the electric field amplitude Er of the scattering light caused by the edge roughness. The polarization characteristic signal of the scattering light, which is caused by the edge roughness and obtained by the inspection optical system illustrated in FIG. 9, can be maintained around the desired value by providing the control system.

In the example of FIG. 11, the desired value becomes zero. Alternatively, the optical image is acquired before the inspection, and the desired value may be decided such that the value ($\sigma/\sqrt{A}$) obtained from the optical image becomes the minimum.

In the embodiment, the value obtained by the following formula is defined as the polarization characteristic signal of the scattering light caused by the edge roughness.

{(first measurement signal)−(second measurement signal)}/{(first measurement signal)+(second measurement signal)}

Therefore, the polarization characteristic signal is not influenced by a reflectance of the substrate in the case that the desired value is not zero in the feedback control. On the other hand, in the case that the desired value is zero, the following formula may be used as the polarization characteristic signal.

(first measurement signal)−(second measurement signal)

An inspection apparatus of the embodiment will be described below.

Figure 13:
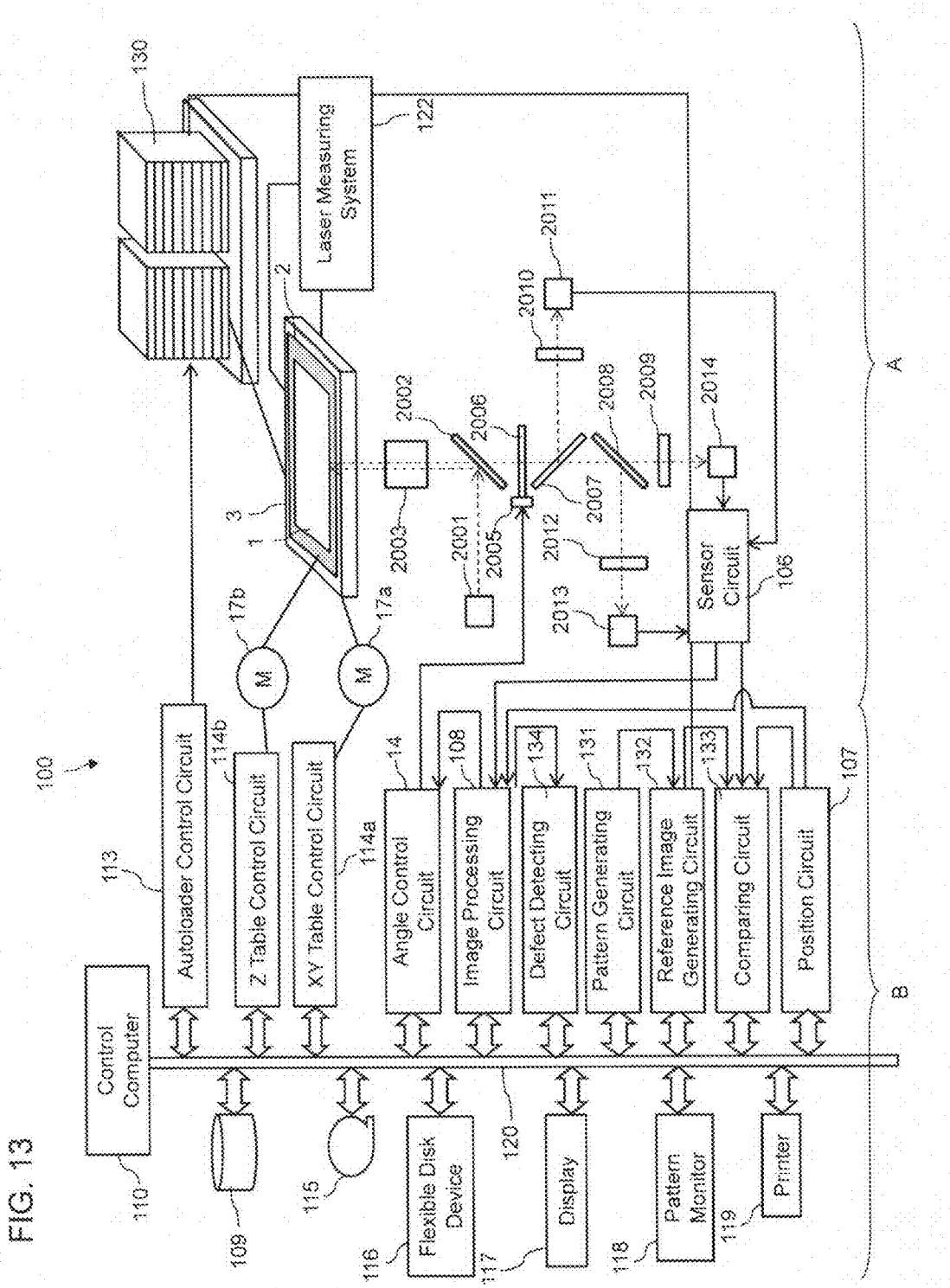
FIG. 13 is a configuration diagram of an inspection apparatus according to the present embodiment.

FIG. 13 is a configuration diagram of an inspection apparatus 100 of the embodiment. The inspection apparatus 100 includes the inspection optical system illustrated in FIG. 9, and has a configuration in which an angle control circuit 14 performs the feedback control described in FIG. 12.

As illustrated in FIG. 13, the inspection apparatus 100 includes an optical image acquisition unit A and a controller B.

The optical image acquisition unit A includes an XY-table 3 that is movable in a horizontal direction (an X direction and a Y direction), a sensor circuit 106, a laser measuring system 122, and an autoloader 130 in addition to the inspection optical system described in FIG. 9. The XY-table 3 may have a structure movable in a rotation direction (θ direction) in addition to the horizontal direction.

A sample 1 that becomes the inspection target is placed on a Z-table 2. The Z-table 2 is provided on the XY-table 3, and is horizontally movable together with the XY-table 3. A repetitive pattern such as the line and space pattern, namely, a regularly repeating pattern having a periodicity is formed on the sample 1. The template used in the nanoimprint technology can be cited as an example of the sample 1.

Preferably the sample 1 is supported at three points using support members provided in the Z-table 2. In the case that the sample 1 is supported at four points, it is necessary to adjust a height of the support member with high accuracy. Unless the height of the support member is sufficiently adjusted, there is a risk of deforming the sample 1. On the other hand, in the three-point support, the sample 1 can be supported while the deformation of the sample 1 is suppressed to the minimum. The supporting member is configured by using a ballpoint having a spherical head surface. For example, the two support members in the three support members are in contact with the sample 1 at two corners, which are not diagonal but adjacent to each other in four corners of the sample 1. The remaining support member in the three support members is disposed in the region between the two corners at which the two other support members are not disposed.

The light source 2001 emits the light to the sample 1 in order to acquire the optical image of the sample 1. A wavelength of the light emitted from the light source 2001 is at least double the pattern pitch. The inspection apparatus 100 is suitable for the inspection of an ultrafine pattern having a line width of 50 to 60 nm or less, and preferably a light source that emits DUV (Deep UltraViolet radiation) light is used as the light source 2001. The use of the DUV light can relatively simply configure the optical system, and inspect the fine pattern with throughput higher than that of an EB (Electron Beam).

The resolution limit of the optical system in the inspection apparatus 100, namely, the resolution limit (R=λ/2NA) defined by the wavelength (λ) of the light emitted from the light source 2001 and a numerical aperture (NA) of the objective lens 2003 is the value that does not resolve the pattern formed on the sample 1.

The light emitted from the light source 2001 is reflected by the half mirror 2002, and the sample 1 that becomes the inspection target is illuminated with the light transmitted through the objective lens 2003. The light reflected by the sample 1 is transmitted through the half-wave plate 2006 including the rotation system 2005 after transmitted through the objective lens 2003 and the half mirror 2002. At this point, the polarization direction of the light rotates by the angle θ'.

The light with which the sample 1 is illuminated is the linearly-polarized light having the polarization plane of 45 degrees with respect to the periodic direction of the periodic pattern formed on the mask. For example, this can be implemented by providing the half-wave plate (not illustrated) between the light source 2001 and the half mirror 2002. Therefore, the difference in sensitivity between the large defect such as the short-circuit defect and the open-circuit defect and the small defect such as the defect caused by the edge roughness can emerge with respect to the electric field component of the illumination light.

The first beam splitter 2007, the second beam splitter 2008, and the inspection analyzer 2009 are disposed in this order in front of the half-wave plate 2006.

The light reflected by the first beam splitter 2007 is transmitted through the first measuring analyzer 2010, and is incident to the first measuring image sensor 2011. On the other hand, part of the light transmitted through the first beam splitter 2007 is reflected by the second beam splitter 2008, transmitted through the second measuring analyzer 2012, and is incident to the second measuring image sensor 2013. The light transmitted through the second beam splitter 2008 is transmitted through the inspection analyzer 2009, and is incident to the inspection image sensor 2014.

The first measuring analyzer 2010, the second measuring analyzer 2012, and the inspection analyzer 2009 differ from one another in the transmission axis direction. The transmission axis direction of the inspection analyzer 2009 is located between the transmission axis direction of the first measuring analyzer 2010 and the transmission axis direction of the second measuring analyzer 2012. Therefore, the quantity of scattering light, which is caused by the edge roughness and transmitted through the half-wave plate 2006 having the angle θ, can be changed between the image acquiring elements. The change in quantity of the scattering light incident to the inspection analyzer 2009 is sandwiched between the change in quantity of the scattering light incident to the first measuring image sensor 2011 and the change in quantity of the scattering light incident to the second measuring image sensor 2013, so that the change in quantity of the scattering light incident to the inspection analyzer 2009 can be correctly obtained.

The controller B in FIG. 13 will be described below.

In the controller B, a control computer 110 that controls the whole inspection apparatus 100 is connected to a position circuit 107, an image processing circuit 108, the angle control circuit 14, an pattern generating circuit 131, a reference image generating circuit 132, a comparing circuit 133, a defect detecting circuit 134, an autoloader control circuit 113, a XY-table control circuit 114a, a Z-table control circuit 114b, a magnetic disk device 109, a magnetic tape device 115, and flexible disk device 116, which are examples of a storage device, a display 117, a pattern monitor 118, and a printer 119 through a bus 120 that constitutes a data transmission line. The image processing circuit 108 corresponds to the image processor of the present invention, the defect detecting circuit 134 corresponds to the defect detector of the present invention, and the angle control circuit 14 corresponds to the angle controller of the present invention.

The Z-table 2 is driven by a motor 17b that is controlled by a Z-table control circuit 114b. The XY-table 3 is driven by a motor 17a that is controlled by an XY-table control circuit 114a. A linear motor, as one example, can be used as each motor.

In the optical image acquisition unit A in FIG. 13, each of the first measuring image sensor 2011, the second measuring image sensor 2013, and the inspection image sensor 2014 acquires the optical image of the sample 1. An example of the specific method for acquiring the optical image will be described below.

The sample 1 is placed on the vertically movable Z-table 2. The Z-table 2 is also horizontally movable by the XY-table 3. The laser measuring system 122 measures a moving position of the XY-table 3, and transmits the moving position to the position circuit 107. The sample 1 on the XY-table 3 is automatically conveyed from the autoloader 130 that is driven by the autoloader control circuit 113, and the sample 1 is automatically discharged after the inspection is ended.

The light source 2001 emits the light illuminated to the sample 1. The light emitted from the light source 2001 is reflected by the half mirror 2002, and focused on the sample 1 using the objective lens 2003. A distance between the objective lens 2003 and the sample 1 is adjusted by perpendicularly moving the Z-table 2.

The light reflected by the sample 1 is transmitted through the half-wave plate 2006 after transmitted through the objective lens 2003 and the half mirror 2002. At this point, the polarization direction of the light rotates by the angle θ'.

Then, the light reflected by the first beam splitter 2007 is transmitted through the first measuring analyzer 2010, and is incident to the first measuring image sensor 2011. On the other hand, part of the light transmitted through the first beam splitter 2007 is reflected by the second beam splitter 2008, transmitted through the second measuring analyzer 2012, and is incident to the second measuring image sensor 2013. The light transmitted through the second beam splitter 2008 is transmitted through the inspection analyzer 2009, and is then incident to the inspection image sensor 2014.

Figure 14:
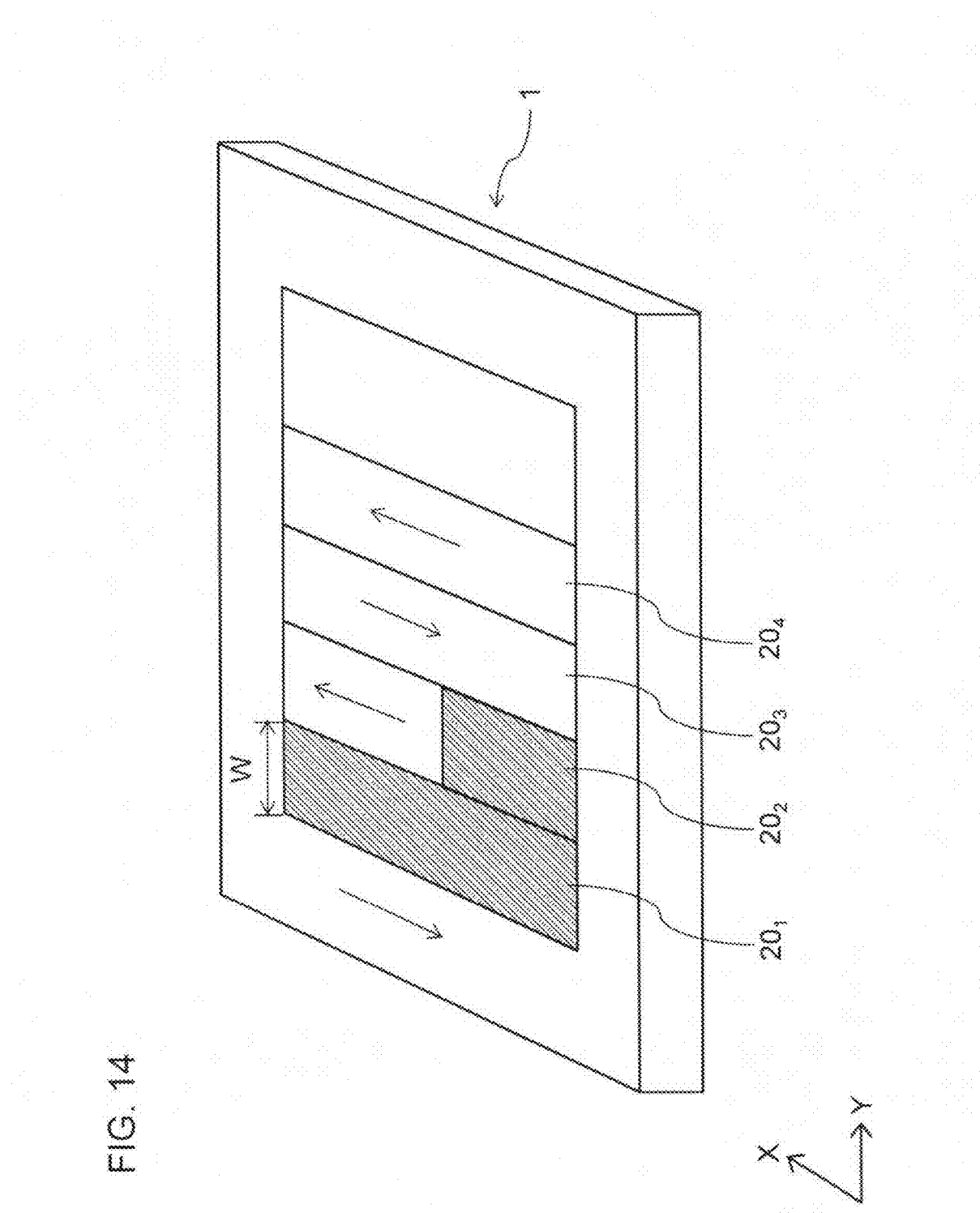
FIG. 14 is a view illustrating a procedure to acquire the optical image of the pattern formed in the sample.

FIG. 14 is a view illustrating a procedure to acquire the optical image of the pattern formed in the sample 1.

As illustrated in FIG. 14, an evaluation region on the sample 1 is virtually divided into plural strip-like frames $20_1$, $20_2$, $20_3$, $20_4$, . . . . The XY-table control circuit 114a controls motion of the XY-table 3 in FIG. 13 such that the frames $20_1$, $20_2$, $20_3$, $20_4$, . . . are continuously scanned. Specifically, the images having a scan width W as illustrated in FIG. 14 are continuously input to each of the first measuring image sensor 2011, the second measuring image sensor 2013, and the inspection image sensor 2014 while the XY-table 3 moves in the X-direction. That is, after the image of the first frame $20_1$ is acquired, the image of the second frame $20_2$ is acquired. In this case, the optical image is acquired while the XY-table 3 moves in the opposite direction to the direction in which the image of the first frame $20_1$ is acquired, and the images having the scan width W are continuously input to each image sensor. In the case that the image of the third frame $20_3$ is acquired, the XY-table 3 moves in the opposite direction to the direction in which the image of the second frame $20_2$ is acquired, namely, the direction in which the image of the first frame $20_1$ is acquired. A hatched-line portion in FIG. 14 schematically expresses the region where the optical image is already acquired in the above way.

After the image of the pattern formed in each of the first measuring image sensor 2011, the second measuring image sensor 2013, and the inspection image sensor 2014 is subjected to photoelectric conversion, the sensor circuit 106 performs A/D (analog-digital) conversion to the image. For example, the line sensor in which CCD cameras that are of the image acquiring elements are arrayed in line is used as each image sensor. A TDI (Time Delay Integration) sensor can be cited as an example of the line sensor. In this case, the image of the pattern in the sample 1 is acquired by the TDI sensor while the XY-table 3 continuously moves in the X-axis direction.

The optical image data to which the sensor circuit 106 performs the A/D conversion is transmitted to the image processing circuit 108. In the image processing circuit 108, the optical image data is expressed by the gray level in each pixel. For example, one of values of a 0 gray level to a 255 gray level is provided to each pixel by a gray scale having 256 gray levels. In the embodiment, the image processing circuit 108 obtains the standard deviation σ of the gray level and the average gray level A with respect to each of the optical images acquired by the first measuring image sensor 2011 and the second measuring image sensor 2013.

It is assumed that the value (σ/√A) obtained from the optical image acquired by the first measuring image sensor 2011 is the first measurement signal, and that the value (σ/√A) obtained from the optical image acquired by the second measuring image sensor 2013 is the second measurement signal. The value obtained by the following formula is defined as the polarization characteristic signal of the scattering light caused by the edge roughness, and the value is plotted with respect to the rotation angle (θ') of the polarized light.

$$\{(\text{first measurement signal}) - (\text{second measurement signal})\} / \{(\text{first measurement signal}) + (\text{second measurement signal})\}$$

As described above, FIG. 11 illustrates the example in which the value obtained from the value ($\sigma/\sqrt{A}$) in each electric field amplitude of the scattering light, which is caused by the edge roughness in each optical image (illustrated in FIG. 10) using the above formula is plotted with respect to the rotation angle ($\theta'$) of the polarized light. As can be seen from the example in FIG. 11, when the electric field amplitude of the scattering light, which is caused by the edge roughness and transmitted through the inspection analyzer 2009, becomes the local minimum, the polarization characteristic signal becomes the value around zero and has the substantially constant gradient around zero. Therefore, in this case, the image processing circuit 108 transmits information indicating that the desired value is zero to the angle control circuit 14, and the angle control circuit 14 controls the polarization direction of the light transmitted through the half-wave plate 2006. Using the rotation system 2005, the angle control circuit 14 adjusts the angle of the half-wave plate 2006, namely, the rotation angle ($\theta'$) of the polarized light transmitted through the half-wave plate 2006 such that the polarization characteristic signal of the scattering light caused by the edge roughness becomes the value around zero.

By controlling the polarization state of the illumination light and the condition of the polarization control element of the optical system forming the image of the light reflected from the sample that becomes the inspection target, the scattering component from the defect caused by the edge roughness can be removed by the polarization control element, and distinguished from the scattering component caused by the short-circuit defect or the open-circuit defect. That is, the defect caused by the edge roughness is removed in the optical image obtained by the inspection image sensor 2014. As described above, the optical image data is transmitted to the image processing circuit 108 through the sensor circuit 106.

In the image processing circuit 108, the pixel data in the optical image (in which the defect caused by the edge roughness is removed) is expressed by the gray level in each pixel. The inspection region of the sample 1 is divided into predetermined unit regions, and the average gray level of each unit region is obtained. For example, the predetermined unit region may be set to the region of 1 mm×1 mm.

The information on the gray level obtained by the image processing circuit 108 is transmitted to the defect detecting circuit 134. For example, the defect detecting circuit 134 has upper and lower thresholds around the average gray level, and has a function of recognizing the gray level as the defect to output the result when the gray level exceeds the threshold. The threshold level is already predetermined.

The inspection apparatus of the embodiment can also have a review function in addition to the inspection function. As used herein, the review means an operation in which an operator determines whether the detected defect becomes a problem.

For example, a coordinate of a point, which is determined to be the defect by the comparing circuit 133 in FIG. 13, and the optical image and a reference image, which become a basis of the defect determination, are transmitted to a review device (not illustrated). The operator performs the review by comparing the reference image that becomes the basis of the defect determination to the optical image including the defect. Specifically, the image of the defect point of the sample 1 is displayed using the optical system illustrated in FIG. 13. At the same time, the judgment condition of the defect determination, and the optical image and a reference image, which become the basis of the defect determination, are displayed on a screen of the control computer 110. The defect information obtained by the review is stored in the magnetic disk device 109.

When at least one defect to be corrected is recognized by the review, the sample 1 and a defect information list are transmitted to a correction apparatus (not illustrated) that is of an external apparatus of the inspection apparatus 100. Because a correction method depends on whether a type of defect is a convex defect or a concave defect, the type of the defect including the differentiation between the convex defect and the concave defect and the coordinate of the defect are added to the defect information list.

In the above example, the line and space pattern is cited as the repetitive pattern. However, the embodiment is not limited to the line and space pattern. The embodiment can be applied to the repetitive patterns such as a hole pattern as long as the repetitive pattern has the period of the resolution limit or less.

As described above, according to the inspection apparatus of the embodiment, even in the sample in which the repetitive pattern having the period of the resolution of the optical system or less is formed, the inspection can be performed while the defect to be detected and otherwise are distinguished from each other. Specifically, the scattering component caused by the edge roughness can be removed, and distinguished from the scattering component caused by the short-circuit defect or the open-circuit defect.

The light source that emits the DUV (Deep UltraViolet radiation) light can be used in the inspection apparatus of the embodiment. Therefore, the inspection can be performed without generating the throughput degradation, which becomes a problem in the case that the EB (Electron Beam) is used as the light source.

The present invention is not limited to the embodiments described and can be implemented in various ways without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all inspection apparatuses employing the elements of the invention and variations thereof, which can be designed by those skilled in the art.

What is claimed is:

1. An inspection apparatus comprising:
an illumination optical system that includes a light source emitting light to illuminate a sample that is an inspection target, the light having a predetermined wavelength and being linearly-polarized light having a polarization plane of an angle outside of −5 degrees to 5 degrees and 85 degrees to 95 degrees with respect to a repetitive direction of a repetitive pattern on the sample;
an imaging optical system that includes:
an inspection image sensor that acquires an optical image of the pattern formed on the sample, and forms an image of the light reflected by or transmitted through the sample on the inspection image sensor using a lens,
a half-wave plate that transmits the light reflected by or transmitted through the sample,
a splitter unit that splits the light, in which a polarization direction is rotated by the half-wave plate, into three directions, a first measuring image sensor to which the light split into a first direction by the splitter unit is incident through a first measuring analyzer, a second measuring image sensor to which the light split into a second direction by the splitter unit is incident through a second measuring analyzer, and an inspection analyzer that is disposed on an optical path to the inspection image sensor, the optical path being a third direction into which the light is split by the splitter unit;

an image processor that obtains an average gray level and a standard deviation in each predetermined unit region of the optical image; and a defect detector that detects a defect of the sample, wherein a resolution limit defined by a wavelength of the light source and a numerical aperture of the lens is a value in which the pattern is not resolved, wherein the first measuring analyzer, the second measuring analyzer, and the inspection analyzer differ from one another in a transmission axis direction, and the transmission axis direction of the inspection analyzer is located between the transmission axis direction of the first measuring analyzer and the transmission axis direction of the second measuring analyzer, wherein the inspection apparatus further comprises an angle controller that controls an angle of the half-wave plate, wherein the image processor acquires a first measurement signal ($\sigma/\sqrt{A}$) from a standard deviation ($\sigma$) of a gray level and an average gray level (A), the standard deviation $\sigma$ representing a magnitude of interference between a scatter component and a specular component in a corresponding image with respect to which the standard deviation $\sigma$ is acquired, the average gray level A representing a magnitude the specular component in the corresponding image, the first measurement signal being with respect to the optical image acquired by the first measuring image sensor, and acquires a second measurement signal ($\sigma/\sqrt{A}$) from the standard deviation ($\sigma$) of a gray level and an average gray level (A) with respect to the optical image acquired by the second measuring image sensor, calculates a polarization characteristic signal defined by a formula (1), {(first measurement signal)−(second measurement signal)}/{(first measurement signal)+(second measurement signal)},     formula (1):

rotates the half-wave plate before inspection, obtains a value of the polarization characteristic signal when the measurement signal ($\sigma/\sqrt{A}$) becomes a minimum in the optical image acquired by the inspection image sensor, sets the value to a desired value, and transmits the desired value to the angle controller, and wherein the angle controller controls the angle of the half-wave plate such that the polarization characteristic signal defined by the formula (1) becomes the desired value.

2. The inspection apparatus according to claim 1, wherein the half-wave plate has a structure in which the angle thereof can arbitrarily be adjusted by a rotation system, and the angle controller controls the rotation system.

3. The inspection apparatus according to claim 1, wherein
the splitter unit includes a first beam splitter and a second beam splitter,
the light reflected by the first beam splitter is incident to the first measuring image sensor through the first measuring analyzer,
the light, which is transmitted through the first beam splitter and reflected by the second beam splitter, is incident to the second measuring image sensor through the second measuring analyzer, and
the light transmitted through the first beam splitter and the second beam splitter is incident to the inspection image sensor through the inspection analyzer.

4. The inspection apparatus according to claim 1, wherein the light source emits deep ultraviolet radiation light.

5. The inspection apparatus according to claim 1, further comprising a comparison unit that compares the optical image acquired by the inspection image sensor to a standard image, and determines that a defect exists when a difference value between the optical image and the standard image exceeds a predetermined threshold.

6. The inspection apparatus according to claim 5, further comprising:
a reference image producing unit that produces a reference image, wherein
the standard image is the reference image that is produced from design data of the pattern, and
the reference image produced by the reference image producing unit is transmitted to the comparison unit.

7. The inspection apparatus according to claim 1, wherein the angle of the half wave plate is adjusted to minimize the standard deviation of the gray level.

8. The inspection apparatus according to claim 1, wherein the angle of the first measuring analyzer is adjusted to minimize the standard deviation of the gray level.

9. The inspection apparatus according to claim 1, wherein the angle of the second measuring analyzer is adjusted to minimize the standard deviation of the gray level.

* * * * *